(12) United States Patent
Rytky

(10) Patent No.: US 6,553,247 B1
(45) Date of Patent: Apr. 22, 2003

(54) ELECTRODE BELT OF HEART RATE MONITOR

(75) Inventor: Pekka Rytky, Oulu (FI)

(73) Assignee: Polar Electro Oy, Kempele (FI)

( * ) Notice: Subject to any disclaimer, the term of this patent is extended or adjusted under 35 U.S.C. 154(b) by 251 days.

(21) Appl. No.: 09/679,028

(22) Filed: Oct. 4, 2000

(30) Foreign Application Priority Data

Oct. 4, 1999 (FI) .............................................. 19992136

(51) Int. Cl.[7] .................................................. A61B 5/04
(52) U.S. Cl. ...................... 600/386; 600/372; 600/513; 128/905; 128/925
(58) Field of Search ................................ 600/386–390, 600/384, 391–393, 501, 513, 372; 128/905, 925

(56) References Cited

U.S. PATENT DOCUMENTS

| 4,815,472 A | 3/1989 | Wise et al. |
| 4,928,690 A * | 5/1990 | Heilman et al. ............ 128/421 |
| 5,134,281 A | 7/1992 | Bryenton et al. |
| 5,184,620 A | 2/1993 | Cudahy et al. |
| 5,191,886 A | 3/1993 | Paeth et al. |
| 5,778,880 A | 7/1998 | Chen |
| 6,272,365 B1 * | 8/2001 | Ronkainen et al. ......... 600/390 |

FOREIGN PATENT DOCUMENTS

| DE | 9216805 U | 2/1993 |
| EP | 0509689 A2 | 10/1992 |
| FI | U990232 | 9/1999 |
| WO | WO 93/10706 | 6/1993 |

* cited by examiner

Primary Examiner—Tony M. Argenbright
Assistant Examiner—Johnny H. Hoang
(74) Attorney, Agent, or Firm—Hoffmann & Baron, LLP (57) ABSTRACT

An electrode belt of a heart rate monitor, the electrode belt comprising one or more electrodes for measuring the heart rate on the chest, an electronics unit for handling the information to be received from the electrode, a conductor for providing electrical contact between the electronics unit and the electrode, at least one wavelike supporting structure provided with alternating upwards and downwards directing sections and intended for protecting the conductor. The conductor of the electrode belt follows the shape of the supporting structure, thus having a wavelike form.

19 Claims, 5 Drawing Sheets

ELECTRODE BELT OF HEART RATE MONITOR

FIELD OF THE INVENTION

The invention relates to an electrode belt of a heart rate monitor, which belt is to be placed on the chest. A heart rate monitor is a device used in sports and medicine, the device measuring the human heart rate on the chest or at the wrist.

BACKGROUND OF THE INVENTION

An electrode belt which belongs to a heart rate monitor and is to be placed on the chest is known to have such a structure that there is an electronics unit at the central portion of the belt and an electrode on both sides of the electronics unit. The electrodes measure the electric pulse of the heart and transmit the measurement result to the electronics unit via a conductor combining the electrode and the electronics unit. Components included in the electrode belt, such as the electronics unit and electrodes, are coated with plastic or rubber in order to protect the components from humidity, for instance. Depending on the structure of the electrode belt, the electronics unit often also comprises means for transmitting an electric pulse as an analogous burst to a receiver and display unit at the wrist, for example. Alternatively the electrode belt itself may contain means for storing and displaying the electric pulses.

Usually electrode belts have such a structure that a rubber or plastic supporting structure coating the components of the electrode belt is relatively rigid between the electronics unit and the electrodes. Such electrode belts are not very well suited for slim adults and children, since the electrode belt does not bend and adapt well enough to a body of a person with a narrow chest. In some of the prior art solutions, the problem has been approached such that the plastic supporting structure between the electronics unit and the electrode has an accordion-like shape, in which case the electrode belt can be bent immediately from outside the electronics unit. In the known solutions, the conductor combining the electronics unit and the electrode is a straight section inside the supporting structure having an accordion-like shape. The prior art solution is illustrated by FIG. 4B. It can be seen from the figure that a conductor 304 extends as a separate section along a supporting structure 300A/300B and pierces the supporting structure in point 412 illustrated by a broken line.

The prior art solution includes a serious weakness: when the accordion-like supporting structure is bent or stretched, there is a big risk of the conductor to be damaged or come loose from the electronics unit or the electrode.

BRIEF DESCRIPTION OF THE INVENTION

The object of the invention is to implement an improved structure of an electrode belt. This is achieved by an electrode belt of a heart rate monitor, which is described in the following. It deals with an electrode belt of a heart rate monitor, the electrode belt comprising one or more electrodes for measuring the heart rate on the chest, an electronics unit for handling the information to be received from the electrode, a conductor for providing electrical contact between the electronics unit and the electrode, at least one wavelike supporting structure provided with alternating upwards and downwards directing sections and intended for protecting the conductor. The conductor protected by the supporting structure of the electrode belt follows the shape of the supporting structure, thus having a wavelike form.

The preferred embodiments of the invention are disclosed in the dependent claims.

The invention relates to an electrode belt of a heart rate monitor. In the specification of the invention, the electrode belt refers to a substantially belt-like structure, whereby the length of the belt to be wound around the chest is substantially greater than the width of the belt. Viewed from the side of the electrodes, the length of an electrode belt is typically 5 to 10 times greater than its width, although the invention is naturally not restricted to the fact how much bigger the length is compared to the width. According to a preferred embodiment, the electrode belt comprises means for transmitting heart rate information to a receiver unit to be held at the wrist, the receiver unit possibly also comprising display means for displaying the heart rate information. If the electrode belt comprises the means for transmitting the heart rate information to a receiver, such as a receiver at the wrist or an external computer, the electrode belt is called a transmitter electrode belt. The invention is not, however, restricted to the fact whether or not the electrode belt comprises transmitter electronics. The electrode belt itself may comprise memory means for storing heart rate information and/or display means for displaying the heart rate. However, the invention is not restricted to the fact whether the electrode belt itself comprises the memory means for storing heart rate information or whether the electrode belt comprises the display means for displaying the measured heart rate information. The invention is not restricted to the fact either, how many electrodes the electrode belt contains. According to a preferred embodiment, there are two electrodes, one on each side of the transmitter electronics, but also other solutions are possible. The invention is not restricted to the fact either, which material the coating, i.e. the supporting structure protecting the components of the electrode belt is made of. According to a preferred embodiment, the supporting structure is made of plastic, but it may also be made of rubber or a similar material that is easy to shape.

In accordance with the invention, the supporting structure between the electronics and the electrodes in the electrode belt of a heart rate monitor, which belt is to be placed on the chest, is made of an elastic material to provide the supporting structure with a flexible and wavelike shape with alternating upwards and downwards directing sections. The conductor which is to be found inside the supporting structure between the electrode and the electronics unit and which provides electrical contact follows the shape of the supporting structure and thus has a wavelike shape. In accordance with the invention, the conductor adapts to the wavelike shape of the supporting structure. According to a preferred embodiment, the conductor is placed into the middle of the supporting structure, which means that the distance from the conductor to a first surface of the supporting structure substantially equals to the distance from the conductor to a second surface of the supporting structure.

According to a preferred embodiment of the invention, the conductor inside the supporting structure is built onto a conduction base to support the conductor. The conductor made of an electrically conductive material can be built onto the conduction base by using known manufacturing methods, e.g. by pressing. The cross-section of the conductor is preferably round, but it can also have a strip-like or, when pressed onto a conduction base, a planar shape. The conduction base is formed from a flexible material, such as polyimide, polyethylene, polycarbonate or the like, preferably into a thin film. In the manufacturing stage at which an electrode belt is being molded, the conduction base is preferably formed to follow the wavelike shape of the supporting structure. According to a preferred embodiment, the conduction base of the electrode belt, functioning as a plate supporting the conductor, is a uniform piece, and thus both electrodes are connected to it and the conduction base extends through the electronics unit.

The wavelike shape of the supporting structure, conductor and conduction base according to the invention preferably means that this wavelike shape comprises at least one wave ridge and at least one wave trough. Preferably said wavelike shape is substantially a sine curve. According to a preferred embodiment, the shape becomes wavelike at the edge of the electronics unit, wherefore the belt can be bent immediately from the edge of the electronics unit. When the electrode belt is viewed from the side, i.e. from the level of the electrodes on the long side of the belt, the wavelike shape of the electrode belt can be seen. The supporting structure comprises a first surface on the side where the electrode of the electrode belt is, and a second surface on the opposite side of the first surface of the supporting structure, i.e. on the side that is to be placed away from the body. In a preferred embodiment, the wavelike shape of the electrode belt means that the distance between the first surface and the second surface of the supporting structure, measured perpendicularly from the first surface to the second surface, is substantially constant between two successive wave ridges of the wavelike shape of the supporting structure. The known solutions disclose that the wavelike shape only extends to one side of the belt, for example to the second surface of the supporting structure. Such a solution is for example an electrode belt disclosed in the publication U.S. Pat. No. 5,778,880, which comprises a stepwise slanting fastening strap 3 but a conductive plate 4 of which has a rigid structure. Thereby the stepwise shape is only to be found on the outer surface that is directed away from the body. No actual function is mentioned for the stepwise shape of the fastening strap in the publication; apparently it simply deals with a design feature.

The solution of the invention also differs from solutions in which the upper and lower surface of the supporting structures are wavelike, but the thickness of the supporting structure is not substantially constant. In other words, this section of the supporting structure is entirely pleated on its both sides in a wavelike manner. In the above solutions the conductor does not follow the shape of the supporting structure, but is substantially a straight section inside the supporting structure. In a preferred embodiment of the invention, the wavelike section between the electrode and the electronics unit is symmetrical so that when there is a ridge on the first surface of the supporting structure, there is a trough on the second surface. And vice versa, when there is a trough on the first surface, there is a ridge on the second surface. When the wavelike shape thus extends symmetrically on both surfaces of the supporting structure, the distance between two ridges on the first surface preferably equals to the distance between two troughs on the second surface, which correspond to said ridges.

The invention provides the advantage that the conductor following the shape of the supporting structure of the electrode belt is not at risk of stretching or coming loose from its ends when the electrode belt is bent or stretched.

BRIEF DESCRIPTION OF THE DRAWINGS

In the following the invention will be described in greater detail with reference to the attached drawings, in which.

DESCRIPTION OF EMBODIMENTS

Figure 1:
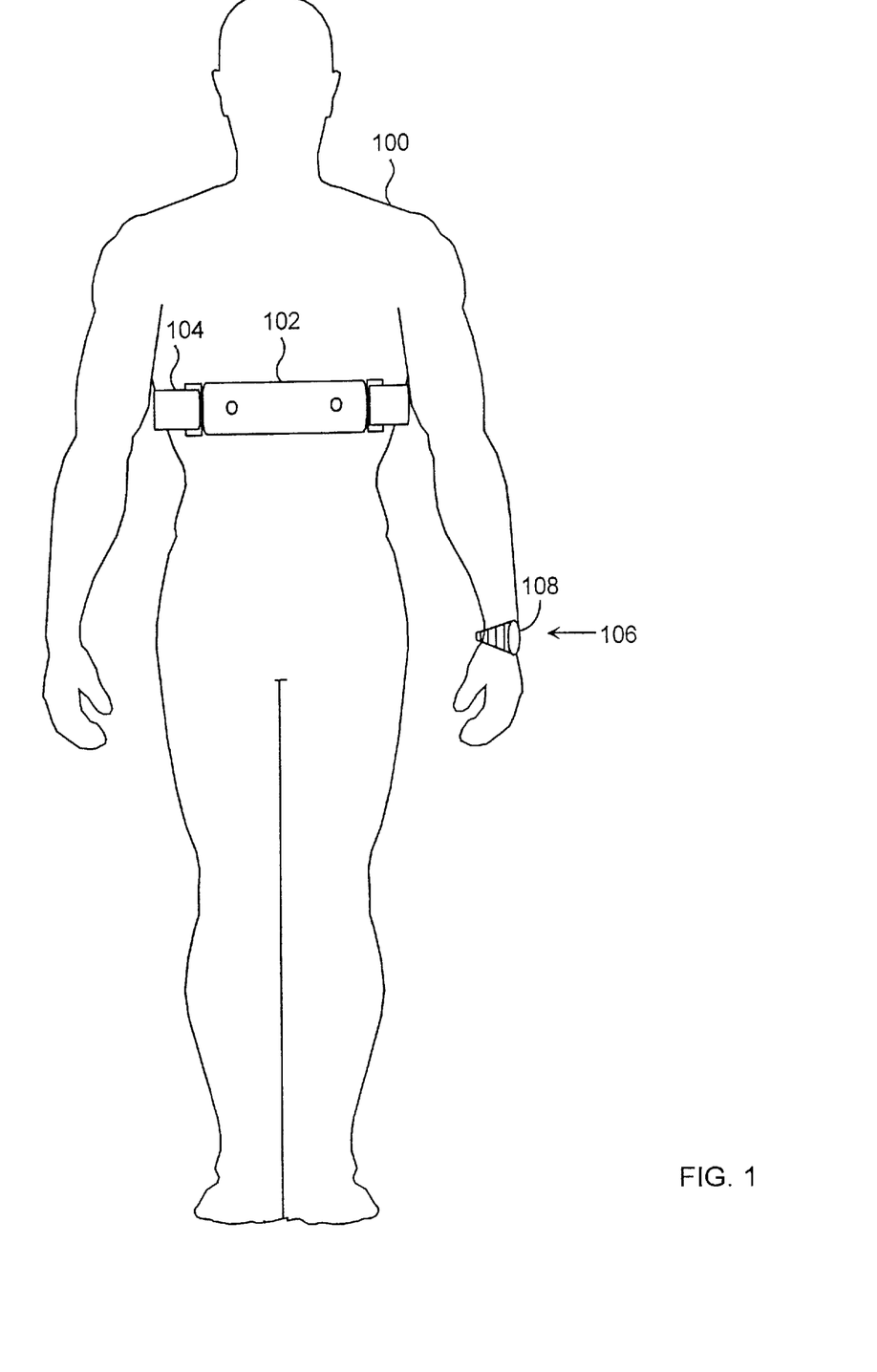
FIG. 1 shows a transmitter electrode belt placed on a person's chest and a receiver unit placed at the wrist.

In the following the invention will be described by means of preferred embodiments with reference to the attached FIGS. 1 to 4. FIG. 1 shows a person 100 whose heart rate is measured by means of a transmitter electrode belt 102 to be placed on the chest. The heart rate is measured by means of two or more electrodes in the transmitter electrode belt 102, between which electrodes a potential difference is formed when the heart beats. The transmitter electrode belt 102 is fastened around the body by means of an elastic strap 104 made of an elastic material, for example. The measured heart rate information is transmitted inductively, for instance, to a receiver 106 at the wrist, the receiver also comprising means 108 for displaying the measured heart rate. The heart rate information can be in such a form that the person's heart rate is already calculated, or each heart beat can be transmitted as one or more bursts to the receiver calculating the heart rate. Alternatively heart rate monitors have been implemented such that the electrode belt 102 on the chest not only measures the heart rate but also calculates, stores, processes and displays the heart rate value, whereupon there is no need for a separate receiver 106 to be placed at the wrist.

Figure 2A:
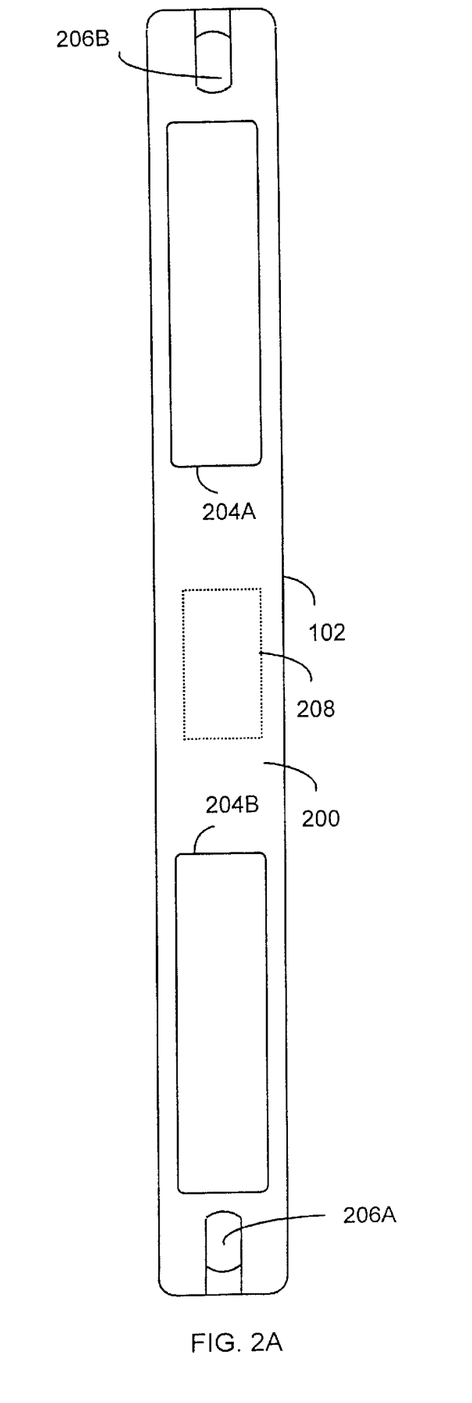
FIG. 2A shows the electrode belt according to FIG. 1, viewed from the side that is to be placed against the body of a person whose heart rate is to be measured.
Figure 2B:
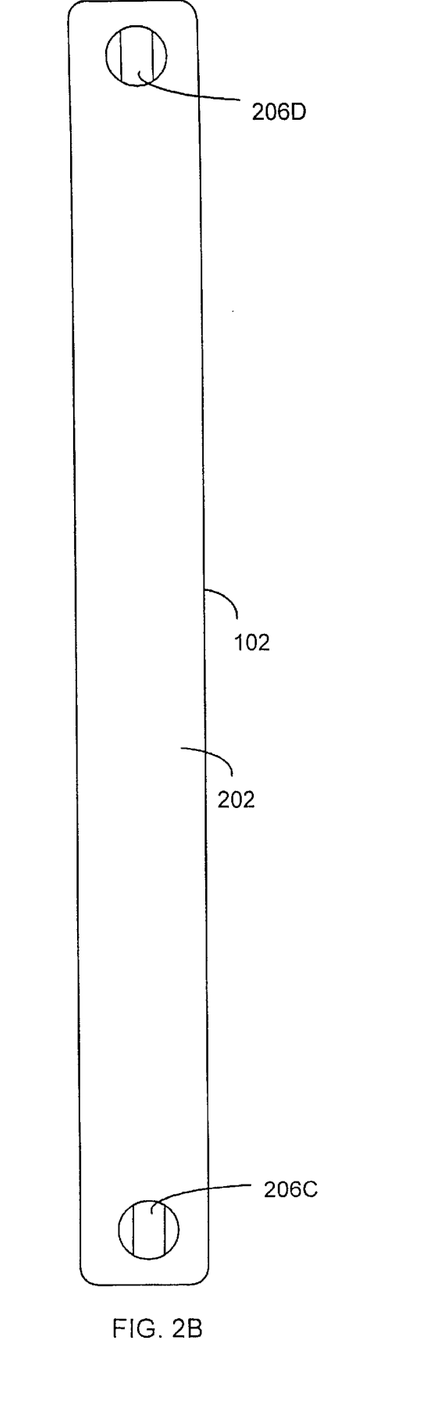
FIG. 2B shows the electrode belt according to an embodiment of the invention, viewed from its outer side, i.e. from the opposite side of the side to be placed against the body of a person to be measured.

FIGS. 2A and 2B show the electrode belt 102 of FIG. 1 in greater detail. In FIG. 2A, the electrode belt 102 is viewed from the side 200 where electrodes 204A to 204B are, i.e. from the side to be placed against the body, and in FIG. 2B, from the side 202 that is to be placed away from the body. The electrode belt 102 of FIG. 2A comprises two electrodes, 204A and 204B. The figure also shows fastening means 206A to 206D by which the electrode belt 102 can be attached to the elastic strap 104 shown in FIG. 1 and intended to be fastened around the body. The fastening means 206A to 206D are preferably casing slots in the electrode belt 102, into which slots button portions in the elastic strap 104 can be positioned. Further, an electronics unit 208 for handling the information obtained from the electrodes 204A to 204B is shown by means of a broken line in FIG. 2A. The operation of the electronics unit 208 is not central to the invention, but it can be stated that one embodiment of the electronics unit 208 comprises e.g. means for receiving a signal from the electrodes, means for detecting a heart rate from the received signal, means for storing heart rate information and means for transmitting the heart rate information inductively to the receiver 106 at the wrist. It can be seen from FIG. 2A that in a preferred embodiment, the electrode belt 102 is a uniform piece, i.e. the elements, such as the electrodes 204A to 204B and the electronics unit 208, are coated with plastic or a similar material keeping the elements together. It is obvious to a person skilled in the art that the electrode belt also comprises other elements than what are shown in FIGS. 2A and 2B. Other essential elements of the invention are described in greater detail in FIGS. 3A to 4C.

Figure 3A:
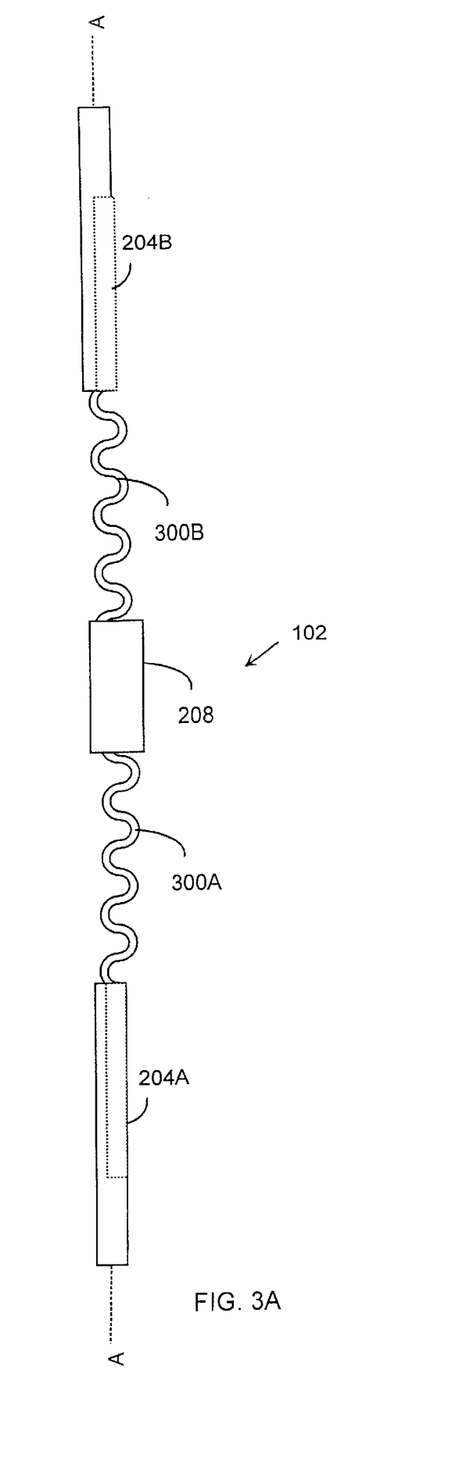
FIG. 3A shows a side view of the electrode belt according to an embodiment of the invention.
Figure 3B:
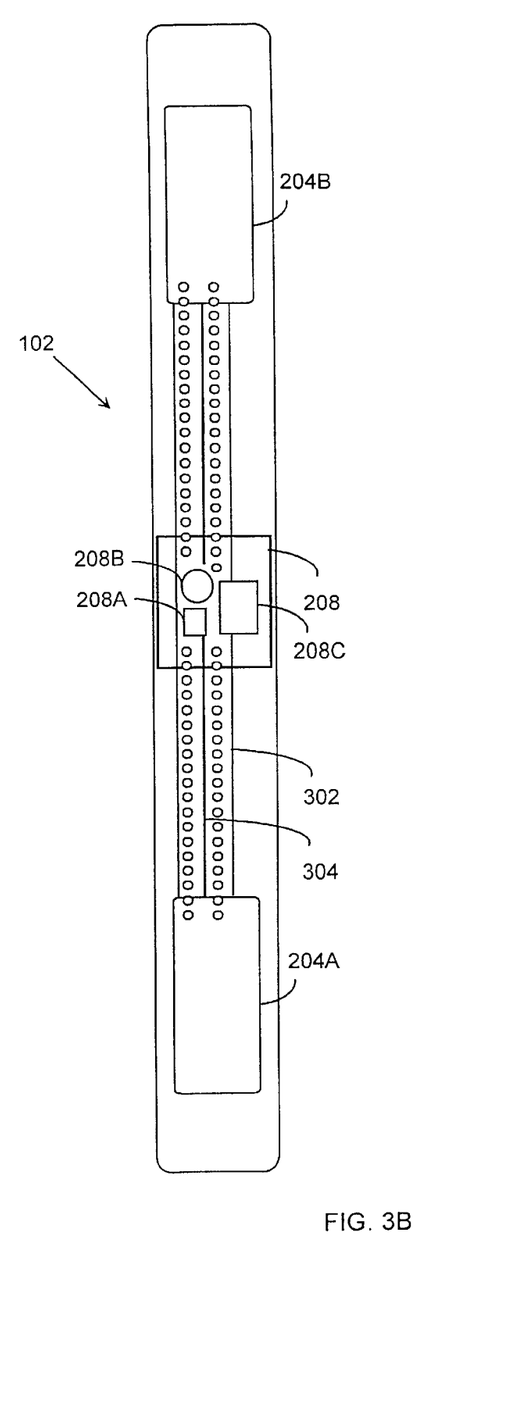
FIG. 3B shows a sectional view of the electrode belt of FIG. 3A.

FIG. 3A illustrates a preferred embodiment of the electrode belt according to the invention. The electrode belt 102 is viewed from its long side, wherefore the electrodes 204A to 204B cannot be seen, but they are marked with a broken line in the figure. The electrode 204A is connected to the electronics unit 208 by a supporting structure 300A and the electrode 204B is connected to the electronics unit 208 by a supporting structure 300B. The figure shows that the supporting structures 300A to 300B have a wavelike shape. Inside the supporting structures 300A to 300B there is a conductor 304 that can be seen in FIG. 3B, the conductor providing electrical contact between the electrodes 204A to 204B and the electronics unit 208. The conductor 304 is made of a conductive material, such as metal. In a preferred embodiment of the invention, the conductor 304 is built onto a conduction base 302. The conduction base 302 is preferably made of a flexible material, such as a polyimide film. The conduction base is preferably very thin, for example 0.1 mm. In the preferred embodiment of the invention, the wavelike electrode belt 102 is such that it stretches 5 to 8 mm from both sides of the electronics unit 208, which is a part of the stretching that is required for the belt to remain fastened around the body. Referring to FIGS. 3A and 3B, both the conduction base 302 and the conductor 304 built thereon follow the wavelike shape of the supporting structures 300A and 300B. In the manufacture, it is preferable that the conduction base 302 is made of one piece, which means that the same conduction base 302 extends from the electrode 204A to the second electrode 204B via the electronics unit 208. At the manufacturing stage, the conduction base 302 preferably functions as a connecting plate for electronic components 208A to 208C of the electronics unit 208, which means that the components 208A to 208C are connected to the conduction base 302 at the manufacturing stage. By way of example FIG. 3B shows a signal amplifier 208A which amplifies the heart rate signal that it has received from the electrode 204A. A battery 208B provides the components of the electronics unit 208 with current. An embodiment of the electronics unit 208 also comprises a transmitter coil 208C for transmitting heart rate information to a receiver that is held at the wrist, for instance. It is obvious to a person skilled in the art that the electronics unit 208 also comprises other components than what are mentioned above, but their description is not essential to the invention.

Figure 3C:
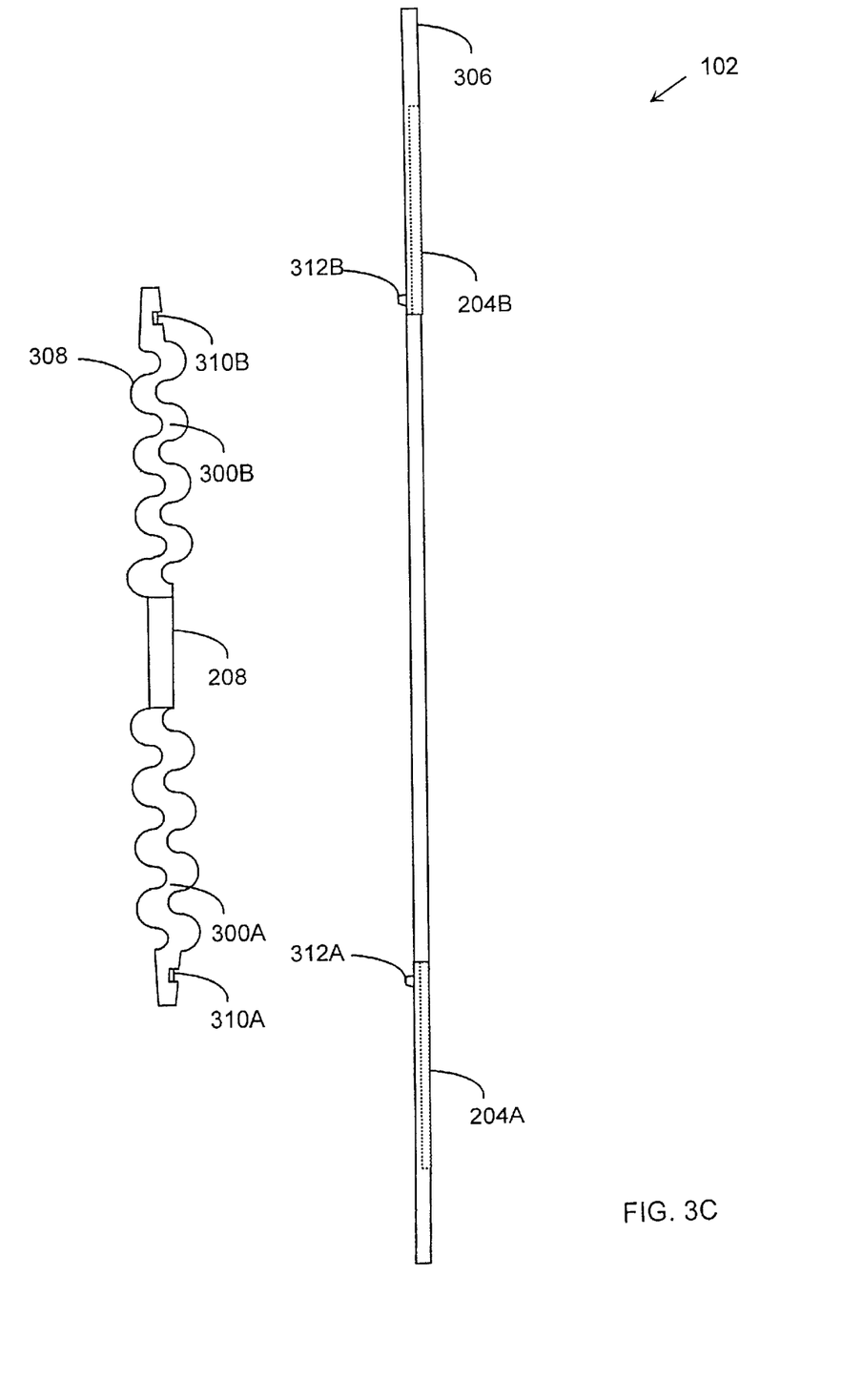
FIG. 3C shows an embodiment of a two-piece electrode belt.

FIG. 3C shows a preferred embodiment of a two-piece electrode belt 102. The invention is not restricted to the fact that the electrode belt 102 is a uniform piece as in FIGS. 3A and 3B, but the electrode belt 102 can also comprise two pieces, i.e. an electrode part 306 and an electronic part 308, which can be attached to each other detachably. The electrode part 306 comprises first fastening means 312A to 312B, which are preferably boss-like projections. The electronic part 308, on the other hand, comprises fastening means 310A to 310B resembling casings, to which the boss-like projections of the electrode part can be positioned such that the first fastening means 312A are positioned into the second fastening means 310A and the first fastening means 312B are positioned into the second fastening means 310B. The first fastening means 312A to 312B and the second fastening means 310A to 310B can also be implemented in another corresponding manner, such as by means of a strip and a slot into which the strip can be positioned. In the solution of FIG. 3C, for example, there is an electrical connection from the electrode 204B to the first fastening means 312B. When the electrode part is connected to the electronic part, the electrical connection proceeds from the first fastening means 312B to the second fastening means 310B, from which it further proceeds via a conductor (not shown in FIG. 3B) comprised in the electronic part 308 to the electronics unit 208. Although the electrode part 306 is shown as a uniform piece in FIG. 3C, it is obvious that it may also consist of two separate parts, the first part comprising the electrode 204A and the second part comprising the electrode 204B.

Figure 4A:
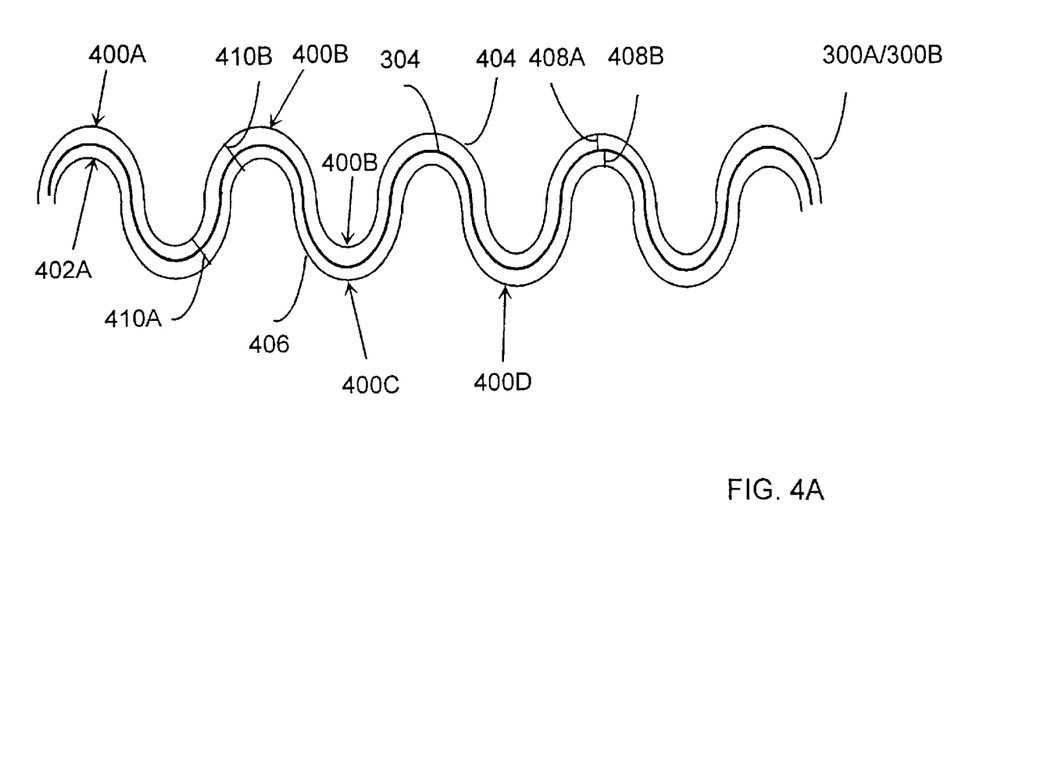
FIG. 4A shows the wavelike shape of a supporting structure that is shown in FIG. 3A.
Figure 4B:
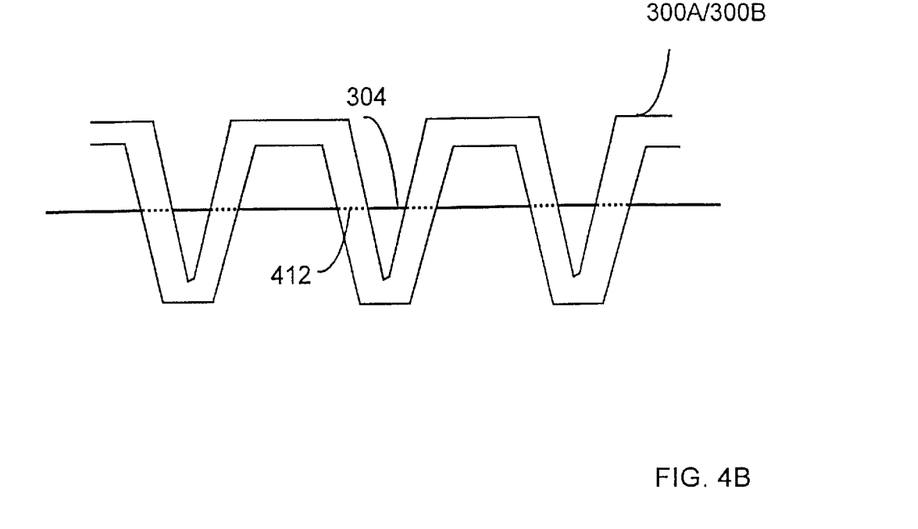
FIG. 4B illustrates prior art solutions to the wavelike shape of a supporting structure.

FIG. 4A illustrates in greater detail what is meant by the wavelike shape of the supporting structures 300A and 300B shown in FIG. 3A. It is obvious that the invention is not restricted to the fact whether the electrode belt 102 has a wavelike supporting structure 300A to 300B on both sides of the electronics unit 208 or whether the wavelike supporting structure 300A to 300B is only to be found on one side of the electronics unit 208, for instance. In FIG. 4A, the electrode belt 102 is viewed from the side, as in FIG. 3A. When it is referred to a wavelike shape of the supporting structure 300A to 300B in the following, it is also thereby referred to the wavelike shape of the conductor 304 inside the supporting structure 300A to 300B and the wavelike shape of the conduction base 302 which is possibly inside it, too. This is due to the fact that, in accordance with a preferred embodiment of the invention, the conductor 304 and the conduction base 302 substantially adapt to the shape of the supporting structure 300A to 300B. In a preferred embodiment of the invention, the supporting structure 300A to 300B has substantially a shape of a sine curve, and thus it comprises alternating upwards and downwards directing sections.

The ridge sections of the wavelike shape of the supporting structure 300A to 3008 are called ridges 400A to 400D in the following, and the trough sections of the wavelike shape of the supporting structure are called troughs 402A to 402B. Each situation is viewed from the respective surface, i.e. the trough 402A on the second surface corresponds to the ridge section 400A on the first surface 404, and the trough 400B on the first surface corresponds to the ridge section 400C on the second surface. The wavelike shape of the conductor 304 can be regarded to follow the wavelike shape of the first surface 404, i.e. when the supporting structure 300A to 300B is viewed according to FIG. 4A from the side, the ridges 400A to 400B on the first surface 404 are also located in the ridge section of the conductor 304. Correspondingly, this applies to the trough sections as well. According to a preferred embodiment there is at least one ridge 400A to 400D and at least one trough 402A to 402B in both supporting structures 300A to 300B. This applies naturally to both surfaces 404 and 406, since the surfaces are symmetrical in regard to each other. The supporting structure 300A to 300B further comprises the first surface 404 and the second surface 406. The distance between two successive ridges 400A to 400B of the supporting structure 300A to 300B substantially equals to the distance between two successive troughs 402A to 402B. Preferably the conductor 304 is to be found substantially at the central portion of the supporting structure 300A to 300B, whereupon it is best protected in the supporting structure. In this case, the distance 408A from the conductor to the first surface 404 substantially equals to the distance 408B from the conductor to the second surface 406. In a preferred embodiment, the wavelike shape also means that the thickness of the supporting structure 410A and 410B remains substantially constant between the ridge and the adjacent trough. The thickness 410A to 410B can be measured as a perpendicular distance, for instance, from the first surface 404 to the second surface 406.

Although the invention has been described above with reference to the examples according to the attached drawings, it is to be understood that the invention is not restricted thereto, but may be modified in a variety of ways within the scope of the inventive idea disclosed in the attached claims.

I claim:

1. An electrode belt of a heart rate monitor, the electrode belt comprising:
    at least one electrode for measuring heart rate information,
    an electronics unit for processing the heart rate information received from the at least one electrode,
    at least one supporting structure having a wavelike shape provided with alternating ridges, the alternating ridges defining a pleated inner surface, for placement against the body of a wearer of the electrode belt, and a pleated outer surface opposite the inner surface, and
    a conductor for providing electrical contact between the electronics unit and the at least one electrode, the conductor being supported by the supporting structure and following the shape of the supporting structure, thus having a wavelike form.

2. An electrode belt as claimed in claim 1, wherein the conductor is a section inside the supporting structure between the electronics unit and the electrode.

3. An electrode belt as claimed in claim 1, wherein the electrode belt comprises a conduction base onto which the conductor is built.

4. An electrode belt as claimed in claim 3, wherein the conduction base is inside the supporting structure and thereby follows the wavelike shape of the supporting structure.

5. An electrode belt as claimed in claim 3, wherein the conduction base is made of a flexible polyimide material.

6. An electrode belt as claimed in claim 3, wherein the conduction base and the conductor extend as a uniform piece from the electronics unit to the electrode.

7. An electrode belt as claimed in claim 3, wherein the conduction base is connected to at least two electrodes and that it is a uniform piece extending from one electrode to the other via the electronics unit.

8. An electrode belt as claimed in claim 3, wherein the electronics unit comprises one or more electronic components and that the conduction base functions as a connecting plate for said one or more electronic components.

9. An electrode belt as claimed in claim 1, wherein the electrode belt is a uniform piece to which one or more electrodes and the electronics unit are fixedly arranged.

10. An electrode belt as claimed in claim 1, wherein the electrode belt comprises a first part and one or more second parts, which first part comprises one or more first fastening means and which second part comprises one or more second fastening means, which first part and second part can be attached to each other detachably such that said first fastening means are attached to the second fastening means.

11. An electrode belt as claimed in claim 10, wherein said first part comprises the electronics unit which is in an electrical connection to one or more first fastening means via the conductor and that said second part comprises one or more electrodes, which electrode is in an electrical connection to the second fastening means.

12. An electrode belt as claimed in claim 1, wherein the electronics unit comprises means for transmitting heart rate information measured by the electrodes to a receiver receiving the heart rate information.

13. An electrode belt as claimed in claim 12, wherein the means for transmitting the heart rate information measured by the electrodes to the receiver receiving the heart rate information comprise a coil for transmitting the heart rate information wirelessly and inductively to the receiver.

14. An electrode belt as claimed in claim 1, wherein the wavelike shape of the supporting structure and the conductor comprises at least one wave ridge and at least one wave trough.

15. An electrode belt as claimed in claim 14, wherein the wavelike shape is substantially a sine curve.

16. An electrode belt as clamed in claim 14, wherein the distance between the pleated inner surface and the pleated outer surface of the supporting structure, measured perpendicularly from the inner surface to the outer surface, is substantially constant between the wave ridge on the inner surface of the wavelike shape of the supporting structure and the wave trough following said wave ridge.

17. An electrode belt as claimed in claim 14, wherein the distance between two successive wave ridges defining the pleated inner surface of the supporting structure substantially equals the distance between two successive wave troughs.

18. An electrode belt as claimed in claim 1, wherein the pleated inner surface and the pleated outer surface of the supporting structure are symmetrical.

19. An electrode belt as claimed in claim 1, wherein the distance from the conductor to the pleated inner surface of the supporting structure substantially equals the distance from the conductor to the pleated outer surface for the supporting structure.

* * * * *

UNITED STATES PATENT AND TRADEMARK OFFICE
CERTIFICATE OF CORRECTION

PATENT NO.    : 6,553,247 B1
DATED         : April 22, 2003
INVENTOR(S)   : Pekka Rytky It is certified that error appears in the above-identified patent and that said Letters Patent is hereby corrected as shown below:

Column 6,
Line 36, now reads "structure 300A to 3008" should read -- structure 300A to 300B --

Signed and Sealed this

Fourteenth Day of October, 2003

JAMES E. ROGAN
*Director of the United States Patent and Trademark Office*